United States Patent [19]
Blake et al.

[11] Patent Number: 5,837,220
[45] Date of Patent: Nov. 17, 1998

[54] METHOD FOR ANALYZING THE IMMUNOSUPPRESSANT ACTIVITY OF ION CHANNEL BLOCKERS USING THE MINI-PIG

[75] Inventors: J. Thomas Blake, Scotch Plains, N.J.; William P. Feeney, Yardley, Pa.; Gloria C. Koo, Woodbridge; Althea D. Talento, Convent Station, both of N.J.

[73] Assignee: Merck & Co., Inc., Rahway, N.J.

[21] Appl. No.: 711,576

[22] Filed: Sep. 10, 1996

Related U.S. Application Data

[60] Provisional application No. 60/003,991 Sep. 19, 1995.
[51] Int. Cl.$^6$ ..................................................... A61K 49/00
[52] U.S. Cl. ............................................. 424/9.2; 424/9.1
[58] Field of Search .............................. 424/9.1, 9.2, 520, 424/529, 900, 278.1; 514/2, 12; 435/4; 530/300, 324

[56] References Cited

U.S. PATENT DOCUMENTS

| | | | |
|---|---|---|---|
| 5,071,964 | 12/1991 | Dustin et al. | 530/395 |
| 5,397,702 | 3/1995 | Cahalan et al. | 435/69.1 |

OTHER PUBLICATIONS

Mix, et al., "Effect on Ion Channel Blockers on Immune Response and Course of Experimental Allergic Neuritis", Allergic Neutritis, Brain, vol. 112, pp. 1405–1418, 1989.

Kaczorowski, et al., "Lymphocyte Ion Channels as a Target for Immunosuppression", Perspectives in Drug Discovery, vol. 2(1), pp. 233–248, 1994.

Koo, et al., Biol. Abstract, vol. 048, Issue 007, 1996.

Lewis, et al., "Potassium and Calcium Channels in Lymphocytes", Ann. Rev. of Immunol., vol. 13, pp. 623–653, 1995.

Lin et al, Voltage–gated potassium channels regulate calcium–dependent pathways involved in human T lymphocyte activation. J. of Exp. Med., vol. 177, No. 3, pp. 637–645, Mar. 1, 1993.

Mallard, B.A., et al., "Genetics and Other Effects on Antibody and Cell Mediated Immune Response in Swine Leucocyte Antigen (SLA) Defined Miniature Pigs", An. Genetics, vol. 20, pp. 167–178, 1989.

Taura, Y., et al., "Fetal Pancreas Translation in Miniature Swine IV. Suppression of DTH and MLR Responses by Treatment with Ultraviolet Light Irradiated Peripheral Blood Lymphocytes", Transplantation, vol. 50(1), pp. 136–140, 1990.

*Primary Examiner*—Jasemine C. Chambers
*Assistant Examiner*—Deborah J. R. Clark
*Attorney, Agent, or Firm*—J. Antonio Garcia-Rivas; Valerie J. Camara; Mark R. Daniel

[57] ABSTRACT

A method for analyzing the immunosuppressant activity of Kv1.3 inhibitors using the mini- and micro-pig. These pig models have been found to have $K_v1.3$ channels very similar to man both in function and setting of membrane potential of T-lymphocytes, and respond similarly in a mixed lymphocyte reaction (MLR) to the $K_v1.3$ channel blockers. The mini-pig and micro-pig provide useful in vivo animal models for studying the immunosuppressant activity of Kv1.3 channel blockers that would be expected to function in man.

10 Claims, 2 Drawing Sheets

METHOD FOR ANALYZING THE IMMUNOSUPPRESSANT ACTIVITY OF ION CHANNEL BLOCKERS USING THE MINI-PIG

BACKGROUND OF THE INVENTION

This application claims the benefit of U.S. Provisional Application No. 60/003,991, filed on Sep. 19, 1995.

The potassium ion channel is involved with the normal cellular homestasis and its possible association with and derangements relating to a variety of disease states and immune responses.

Diseases having a particular association with such channels include autoimmune diseases and transplant rejections. Autoimmune diseases include rheumatoid arthritis, type-1 diabetes mellitus (insulin dependent), multiple sclerosis, myasthenia gravis, systemic lupus erythematosus, Sjorgran's syndrome, mixed connective tissue disease, experimental allergic encephalomyelitis (EAE), to name a few.

In most cases, it is believed that autoimmune diseases result from auto-reactive cells of the immune system destroying target tissues, either by direct killing or by producing autoantibodies. In the autoimmune diseases studied to date, there seems to emerge a common pattern of abnormal immune cells producing materials that either destroy or retard certain target tissues causing symptoms manifest for that disease state.

Allografts or xenografts may be rejected through either a cell-mediated or a humoral immune reaction of the recipient against antigenic components present on rejection which is the acute lymphocyte-mediated immune reaction against transplantation antigens (host vs. graft reaction).

Current treatment for these responses and diseases remains on an empical level and is based on causing a general immunosuppressant response. Such a therapeutic approach is also fraught with other problems including associated severe side effects. Further, they serve only to retard the natural progression of these autoimmune diseases.

Several classes of potassium channels are involved in maintaining membrane potential and regulating cell volume in diverse cell types, as well as modulating electrical excitability in the nervous system. [R. C. Lewis and M. D. Cahalan "Potassium and Calcium Channels in Lymphocytes" Ann. Rev. Immunol. 13, (1995) 623–653 and "Lymphocyte Ion Channels as a Target for Immunosuppression" G. J. Kaczorowski and G. C. Koo Perspectives in Drug Discovery and Design 2, (1994) 233–248.] Potassium channels have been shown to control the repolarization phase of action potentials and the pattern of firing neurons and other cells. Potassium currents have been shown to be more diverse than sodium or calcium currents, and also play a central role in determining the way a cell responds to an external stimulus. For instance, the rate of adaptation or delay with which a neuron responds to synaptic input is strongly determined by the presence of different classes of potassium channnels.

Attention has been focused on the $K^+$ ion channel itself. Two types of ion channel types, classified pharmacologically and electrophysiologically, have been identified, the voltage activated potassium channels ($K_v$) and the calcium activated $K^+$ channels ($K_{Ca}$). T cells in the peripheral lymphoid tissues for present purposes are characterized into relevant types: $CD_4^+CD_8^-$, $CD_4^-CD_8^+$, $CD_4^-CD_8^-$. These cells express some or all of these potassium ion channels. In the normal immune response reflecting induction of activity, such as with mitogens, a single ion channel type is increased upwards of ten fold in the cells that are activated. Thus, normal T cells, when stimulated by mitogens, show a normal immune response elevation in the number of these ion channels.

One of these types of $K^+$ ion channels, Kv1.3, determines membrane potential in non-activated human T-cells. It has been determined that blockade of this $K^+$ ion channel is sufficient to cause depolarization and prevent activation of mitogen. [Lymphocyte Ion Channels as a Target for Immunosuppression" G. J. Kaczorowski and G. C. Koo Perspectives in Drug Discovery and Design 2, (1994) 233–248.]

Prior to the discovery of the mini-pig as an animal model for testing $K_v1.3$ blockers in the mixed lymphocyte reaction, several other animal models were studied, including the mouse, rat, rabbit and guinea pig. However, the mixed lymphocyte reaction is not inhibited by Margatoxin (MgTX), a specific peptide inhibitor of Kv1.3 channels in these animal models. [Leonard et al. Selective blockers of voltage gated $K^+$ channels depolarized human T lymphocytes: mechanism of the antiproliferatice effect of Charybdotoxin. Proc. Natl. Acad. Sci. USA 89: 10094–10098.]

Mini-swine was recently selected to validate the concept that blocking the voltage activated K+ channels (Kv1.3) is a target for immunomodulation. The scorpion toxin, Margatoxin (MgTX) has been shown to block the Kv1.3 channels of the pig T cells in electro-physiological analyses (unpublished communication from Reid Leonard). Margatoxin has also been found to inhibit the mixed lymphocyte reaction in the pig, similar to its effect in human mononuclear cells (MNC). PMA/ionomycin (ION) induced proliferation of pig mononuclear cells was equally inhibited. Therefore in vitro assays indicate that pig Kv1.3 channels are comparable to human Kv1.3 channels in their responses to margatoxin.

T cell mediated delayed type hypersensitivity (DTH) response in the pig was then chosen to test the effect of ion channel blockers in vivo. Margatoxin would be used in DTH, for the lack of specific compound that inhibits the Kv1.3 channels. Therefore, pharmacokinetic (PK) study of margatoxin was conducted in the mini-swine. In addition to determining the concentration of margatoxin in the plasma, we developed an ex vivo assay to assess the response of the mononuclear cells to the induction of PMA and ionomycin (ION) . This assay is currently used to monitor the in vivo biological effect of margatoxin.

SUMMARY OF THE INVENTION

This invention relates to a method for analyzing the immunosuppressant activity of Kv1.3 ion channel blockers using the mini- and micro-pig as the animal model. This invention relates to a method for analyzing an ex vivo effect of an ion channel blocker administered in vivo to a test pig comprising the steps of:
  (a) immunizing the test pig and a control pig with an immunizing antigen;
  (b) measuring the immune response of the test and the control pig;
  (c) administering the ion channel blocker to the test pig;
  (d) administering a vehicle to the control pig;
  (e) measuring the immune response of the test and the control pig;
  (f) challenging the test and the control pig with a challenging antigen;
  (g) measuring the immune response of the test pig relative to the immune response of the control pig; and (h) measuring the antigen response of the test pig and the control pig.

DETAILED DESCRIPTION OF THE INVENTION

Figure 1:
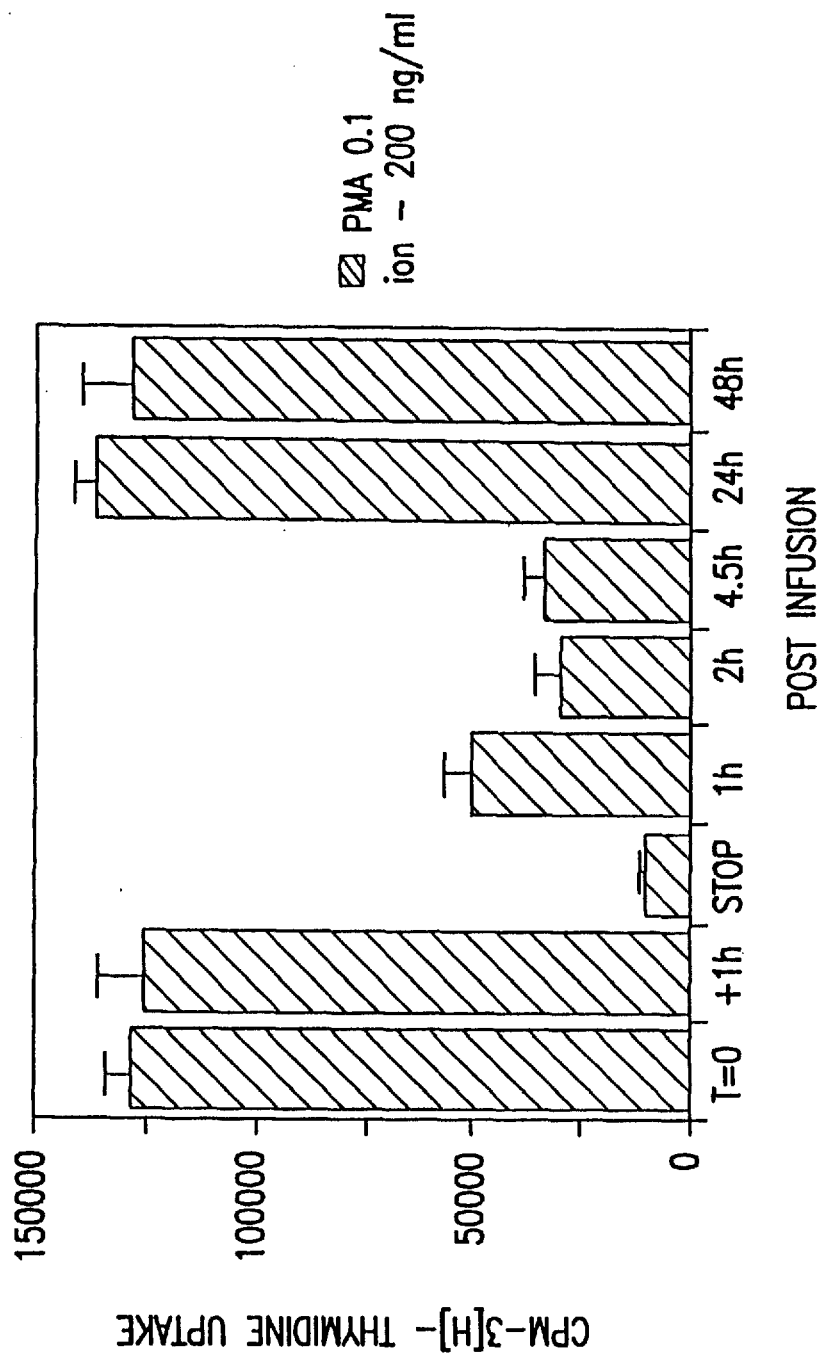
FIG. 1. Pharmacokinetics of Margatoxin: Inhibition of ex vivo PMA/ionomycin-induced proliferation by infusion of 2 $\mu$g/kg of the immunosuppressant, Margatoxin.
Figure 2:
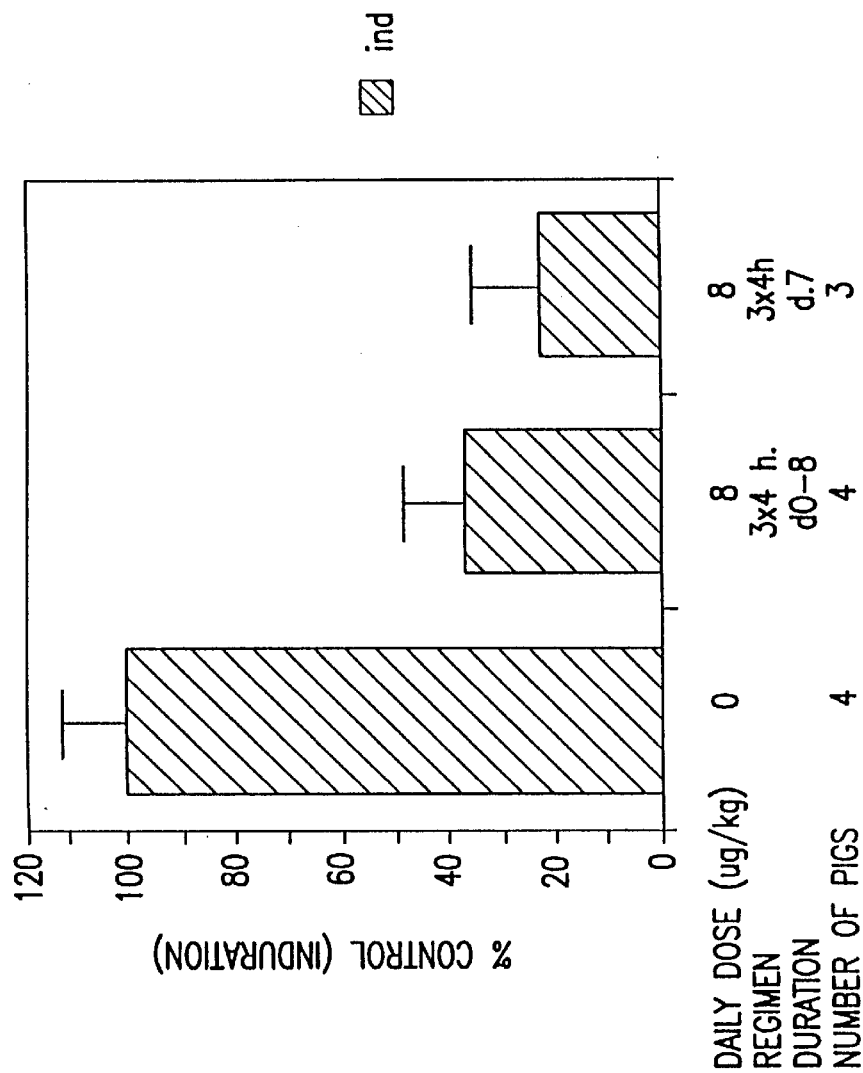
FIG. 2. Inhibition of the delayed type hypersensitivity (DTH) response to Tuberculin (PPD) in the mini-pig.

This invention relates to a method for analyzing an ex vivo effect of an ion channel blocker administered in vivo to a test pig comprising the steps of:

(a) immunizing the test pig and a control pig with an immunizing antigen;

(b) measuring the immune response of the test and the control pig;

(c) administering the ion channel blocker to the test pig;

(d) administering a vehicle to the control pig;

(e) measuring the immune response of the test and the control pig;

(f) challenging the test and the control pig with a challenging antigen;

(g) measuring the immune response of the test pig relative to the immune response of the control pig; and (h) measuring the antigen response of the pig test and the control pig.

An embodiment of the invention is the method as recited above wherein the measurement of the immune response, comprises the steps of:

(a) collecting whole heparinized blood from the pig;
(b) diluting the whole heparinized blood with an equal volume of RPMI;
(c) centrifuging the RPMI-diluted blood solution over ficoll-hypaque;
(d) isolating the mononuclear cell fraction from the centrifuged RPMI-diluted blood solution;
(e) adjusting the concentration of the mononuclear cell fraction to about 2-million cells per mL;
(f) reacting about 100 $\mu$L of a solution of PMA at about 0.1 to 0.5 ng/mL and ionomycin at 200 ng/mL to the microtiter wells with 100 $\mu$L of the mononuclear cells;
(g) incubating the PMA-Ionomycin reaction for about 24 hrs.;
(h) incubating the incubated PMA-ionomycin reaction for an additional 24 hrs. with $^3$H-thymidine;
(i) harvesting the mononuclear cells after incubation with $^3$H-thymidine;
(j) counting the $^3$H-thymidine incorporation into the mononuclear cells.

The above method is used to measure the immunosuppressant activity of the ion channel blocker in mononuclear cells isolated from the blood at various time intervals during the experiment, relative to a control. The samples were prepared without the washing step typically employed when isolating the mononuclear cells from whole heparinized blood, which allowed for rapid detection of the immune responsiveness, after in vivo administration of an ion channel blocker.

This invention also relates to a method for analyzing an ex vivo effect of an ion channel blocker administered in vivo to a test pig comprising the steps of:

(a) immunizing the test pig and a control pig with an immunizing antigen;
(b) measuring the immune response of the test and the control pig comprising the steps of:
   (i) collecting a sample of whole heparinized blood from the test and control pigs;
   (ii) diluting the test and control samples of whole heparinized blood with an equal volume of RPMI;
   (iii) centrifuging the test and control samples of RPMI-diluted blood solution over ficoll-hypaque;
   (iv) isolating the test and control samples of the mononuclear cell fraction from the centrifuged RPMI-diluted blood solution;
   (v) adjusting the concentration of the test and control samples of the mononuclear cell fraction to about 2 million cells per mL;
   (vi) reacting about 100 $\mu$L of a solution of PMA at about 0.1 to 0.5 ng/mL and ionomycin at 200 ng/mL to the microtiter wells with 100 $\mu$L of the test and control samples of the mononuclear cells;
   (vii) incubating the test and control samples of the PMA-ionomycin reaction for about 24 hrs.;
   (viii) incubating the test and control samples of the incubated PMA-ionomycin reaction for an additional 24 hrs. with $^3$H-thymidine;
   (ix) harvesting the test and control samples of the mononuclear cells after incubation with $^3$H-thymidine;
   (x) counting the $^3$H-thymidine incorporation into the test and control samples of the mononuclear cells to establish a baseline;
(c) administering into a vein of the test pig a solution of the ion channel blocker at a dose of about 2 $\mu$g/kg to about 100 mg/kg using an infusion pump dosing at a rate of about 12 mL/hr.;
(d) measuring the immune response of the dosed-test-pig as recited above in step (b);
(e) challenging the test and control pigs with a challenging antigen;
(f) measuring the immune response of the antigen-challenged-test-pig and control pig as recited above in step (b);
(g) measuring the antigen response of the test pig and the control pig.

An embodiment of the invention is the method for analyzing an ex vivo effect of an ion channel blocker administered in vivo to a pig wherein the pig is immunized with Bacillus-Calmette-Guerin and later challenged with purified protein derivative-tuberculin (PPD).

The term pig used in the instant invention include the mini-pig and the micro-pig, the pigs ranging in weight from about 2 kg to about 15 kg. The preferred animal model being the Yucatan mini-pig or the Yucatan micro-pig. Other strains of mini-pigs are Hanford, NIH and Minnesota varieties. The Yucatan mini-pigs and Yucatan micro-pigs were obtained from Charles River, Windham, Me.

The ion channel blocker is administered to the pig either intravenously, orally, intramuscularly or subcutaneously. The preferred route of adminstration is selected from intravenous or oral.

The daily dose of the ion channel blocker is between about 2 $\mu$g/kg to about 100 mg/kg. The preferred daily dose of an ion channel blocker is about 0.1 mg/kg to about 100 mg/kg when administered orally and about 2 $\mu$g/kg to about 15 mg/kg when administered intravenously. Margatoxin has been found to be effective in a range from about 4 $\mu$g/kg to about 8 $\mu$g/kg.

An ambulatory infusion pump (Pharmacia-Delta) or a portable infusion pump was used to deliver the ion channel blocker, e.g. margatoxin, at a pre-programmed rate to the pig. The reservoir within the pump were filled daily with a solution of the ion channel blocker, when the compound was delivered every day. The chosen dose of ion channel blocker was diluted in 30 ml of 1:1 saline and PBS, containing the 5% autologous serum. The pigs were instrumented with catheters at the jugular vein and artery, several days before the assay. At the time of treatment, the ambulatory infusion pump was mounted in the pocket of a custom-made vest, made of polyester net material (Fabric Expression, Seattle, Wash.) or the pig is restrained in a sling during the duration of the study and the intravenous catheter is connected to a portable infusion pump. The margatoxin solution was delivered by an infusion pump, at a rate of about 2 to about 12 ml/hr. The margatoxin solution is infused three times a day dosing over a four hour period and was delivered either on the eight days following the immunization or on the day of the challenge. The pigs were then immunized with 1 mg of Bacillus-Calmette-Guerin (Connaugh) intradermally and subcutaneously at about 4 to about 6 different sites on the rump. On the day (7–10 days post immunization) of challenge, 0.1 ml of tuberculin (PPD) (25 Units, Connaugh) was injected intradermally, when the pig was sedated with Telazol and/or isoflurane. See the timeline set forth below. Induration was measured 48 hrs. later. Blood was collected at various times during and after infusion for biochemical determinations and biological assays, as described below.

PROTOCOL FOR DELAYED TYPE HYPERSENSITIVITY TO PPD-TUBERCULIN WITH i.v. TREATMENT OF MARGATOXIN

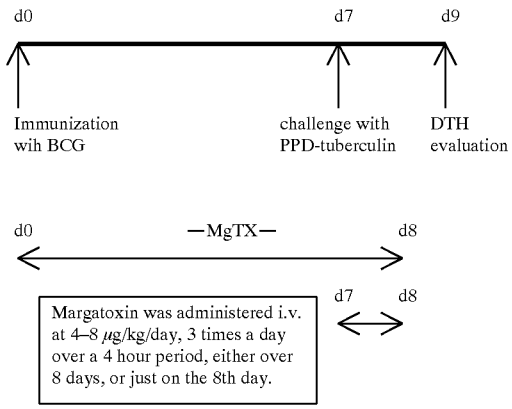

Initially, MgTX was delivered from the day of Bacillus-Calmette-Guerin (BCG) immunization to the day after tuberculin challenge and 50–80% suppression of the response was observed. However, when experiments were carried out to suppress the response by delivering MgTX only on the day of challenge, the same effect was observed.

Whole heparinized blood was collected, diluted with equal volume of RPMI (GIBCO) and centrifuged over ficoll-hypaque (LSM, Organo Technika Co., Durham, N.C.). The mononuclear cell fraction was isolated and adjusted to a concentration of about $2\times10^6$/ml. Then 100 μl of the diluted mononuclear cell fraction was added to each well of a flat-bottom 96-well microtiter plate. 100 μl containing PMA (final concentration of 0.1–0.5 ng/ml) and ionomycin (final concentration of 200 ng/ml) was added. In some assays, where the suppressive effect of margatoxin was tested in vitro, 50 μl of media or margatoxin (final conc. 50–200 nM) was added. The cells were then cultured for 2 days at 37° C. and 7% $CO_2$. [$^3$H]Thymidine was added for the last 24 h. The cells were harvested and thymidine incorporation was counted by the LKB beta plate system.

Prior to conducting the pharmokinetic studies, we have spiked whole blood with Margatoxin and observed significant suppression of the proliferative response to PMA/ION, tested under the conditions described herein. In the pharmokinetic studies, blood samples were taken at the designated times and 1 ml of heparinized blood was spun and the plasma levels of margatoxin were determined. Two ml of blood was separated over ficoll-hypaque, and the MNC were tested for PMA/ION induction, as described above.

A representative experiment is shown in FIG. 1. A Yucatan mini-pig received 25 μg of margatoxin in 30 ml of vehicle (5% autologous serum in 1:1 saline to PBS solution) over 2.5 h. There was no significant rise in blood pressure or heart rate during infusion. Plasma level in this study peaked at 600 pM, at the end of infusion, and dropped to 100 pM at 4.5 h post-infusion, with half-life of about 2 h. Margatoxin was undetectable in the plasma in 24 h. Plasma level of MgTX was determined in a competition binding assay, by its inhibition of $^{125}$I-labeled MgTX binding to Kv1.3 channels present in isolated plasma membranes. Unresponsiveness to PMA/ION was also maximal at the end of infusion, and sustained for 4.5 h post-infusion. Similar pharmokinetic study was performed six times, with good correlations between high plasma levels of margatoxin and the lower response to PMA/ION. Yucatan mini-pigs receiving vehicle had no significant fluctuation of responses to PMA/ION. Therefore, this ex vivo test provides an assessment of the in vivo biological effect of margatoxin and can also be used to study the immunosuppressant effects of other ion channel blockers.

A representative graph of the inhibition by Margatoxin of the delayed type hypersensitivity response to PPD-tuberculin is shown in FIG. 2. The Yucatan mini-pig was immunized with BCG 8 days (−8 d) prior to the challenge with PPD-tuberculin (PPD). MgTX was given on the eight days prior to the challenge or on the day of the challenge (0 d). PPD-tuberculin was injected intradermally at 4–6 spots on the flank of the pig. As control, PBS, the diluent for PPD was injected at 4–6 sites. Measurement of the antigen response, specifically the redness and induration was recorded for both the test and control injection sites at about 44 to 48 hours after the challenge.

What is claimed is:

1. A method for analyzing the immunomodulating effect of a Kv1.3 ion channel blocker administered in vivo to a test pig comprising the steps of:

(a) immunizing the test pig and a control pig with an immunizing antigen;

(b) measuring the mononuclear cell proliferation or delayed-type hypersensitivity (DTH) response of the test pig and that of the control pig to said immunizing antigen;

(c) administering a pharmaceutical preparation of a Kv1.3 ion channel blocker to the test pig;

(d) administering said pharmaceutical preparation without the Kv1.3 ion channel blocker to the control pig;

(e) re-measuring the mononuclear cell proliferation or delayed-type hypersensitivity (DTH) response of the test pig and that of the control pig to said immunizing antigen;

(f) challenging the test pig and the control pig with a challenging antigen;

(g) measuring the mononuclear cell proliferation or delayed-type hypersensitivity (DTH) response of the test pig and that of the control pig to said challenging antigen;

(h) comparing the mononuclear cell proliferation or delayed-type hypersensitivity (DTH) response to said challenging antigen of the test pig to the mononuclear cell proliferation or delayed-type hypersensitivity (DTH) response to said challenging antigen of the control pig, respectively.

2. The method of claim 1, wherein steps (b), (e), or (g) further comprise the steps of:

(a) collecting whole heparinized blood from the pig;

(b) diluting the whole heparinized blood with an equal volume of RPMI;

(c) centrifuging the RPMI-diluted blood solution over ficoll-hypaque;

(d) isolating the mononuclear cell fraction from the centrifuged RPMI-diluted blood solution;

(e) adjusting the concentration of the mononuclear cell fraction to about 2-million cells per mL;

(f) reacting about 100 μL of a solution of PMA at about 0.1 ng/mL to 0.5 ng/mL and ionomycin at 200 ng/mL to the microtiter wells with 100 μL of the mononuclear cells;

(g) incubating the PMA-Ionomycin reaction for about 24 hrs.;

(h) incubating the incubated PMA-ionomycin reaction for an additional 24 hrs. with $^3$H-thymidine;

(i) harvesting the mononuclear cells after incubation with $^3$H-thymidine;

(j) counting the $^3$H-thymidine incorporation into the mononuclear cells.

3. A method for analyzing the immunomodulating effect of a Kv1.3 ion channel blocker administered in vivo to a test pig comprising the steps of:

(a) immunizing the test pig and a control pig with an immunizing antigen;

(b) measuring the mononuclear cell proliferative response of the test pig and that of the control pig to said immunizing antigen by a method comprising the steps of:

(i) collecting a sample of whole heparinized blood from the test pig and control pig;

(ii) diluting the test and control samples of whole heparinized blood with an equal volume of RPMI;

(iii) centrifuging the test and control samples of RPMI-diluted blood solution over ficoll-hypaque;

(iv) isolating the test and control samples of the mononuclear cell fraction from the centrifuged RPMI-diluted blood solution;

(v) adjusting the concentration of the test and control samples of the mononuclear cell fraction to about 2-million cells per mL;

(vi) reacting about 100 μL of a solution of PMA at about 0.1 ng/mL to 0.5 ng/mL and ionomycin at 200 ng/mL to the microtiter wells with 100 μL of the test and control samples of the mononuclear cells;

(vii) incubating the test and control samples of the PMA-ionomycin reaction for about 24 hrs;

(viii) incubating the test and control samples of the incubated PMA-ionomycin reaction for an additional 24 hrs. with $^3$H-thymidine;

(ix) harvesting the test and control samples of the mononuclear cells after incubation with $^3$H-thymidine; and (x) counting the $^3$H-thymidine incorporation into the test and control samples of the mononuclear cells to determine the relative mononuclear proliferative response;

(c) administering into a vein of the test pig a solution of the Kv1.3 ion channel blocker at a daily dose of about 2 μg/kg to about 100 mg/kg using an infusion pump dosing at a rate of about 2.0 mL/hrs. to about 12 mL/hrs.;

(d) re-measuring the mononuclear cell proliferative response to the immunizing antigen of the dosed-test-pig as recited above in step (b);

(e) challenging the test pig and the control pig with a challenging antigen;

(f) measuring the mononuclear cell proliferative response of the antigen-challenged-test-pig and that of the control pig to said challenging antigen as recited above in step (b);

(g) comparing the mononuclear cell proliferative response to said challenging antigen of the test pig to the mononuclear cell proliferative response to said challenging antigen of the control pig, respectively.

4. The method claim 3, wherein the pigs are Yucatan mini-pigs or micro-pigs.

5. The method of claim 4, wherein the pigs are Yucatan mini-pigs or micro-pigs.

6. The method of claim 4, wherein the immunizing antigen used is Bacillus-Calmette-Guerin and the challenging antigen used is PPD-tuberculin.

7. The method of claim 5, wherein the immunizing antigen used is Bacillus-Calmette-Guerin and the challenging antigen used is PPD-tuberculin.

8. The method of claim 7, wherein step (c) comprises oral, intravenous, intramuscular, or subcutaneous administration of the daily dose of the Kv1.3 ion channel blocker.

9. The method of claim 8, wherein step (c) comprises oral administration of a daily dose of the Kv1.3 ion channel blocker, wherein the daily dose is about 0.1 mg/kg to about 100 mg/kg.

10. The method of claim 8, wherein step (c) comprises intravenous administration of a daily dose of the Kv1.3 ion channel blocker, wherein the daily dose is about 2 μg/kg to about 15 mg/kg.

* * * * *